United States Patent [19]
Saadat

[11] Patent Number: 6,010,476
[45] Date of Patent: Jan. 4, 2000

[54] APPARATUS FOR PERFORMING TRANSMYOCARDIAL REVASCULARIZATION

[75] Inventor: Vahid Saadat, Redwood Shores, Calif.

[73] Assignee: AngioTrax, Inc., Sunnyvale, Calif.

[21] Appl. No.: 08/953,769

[22] Filed: Oct. 17, 1997

Related U.S. Application Data

[60] Provisional application No. 60/032,196, Dec. 2, 1996.

[51] Int. Cl.[7] ................................................. A61B 17/32
[52] U.S. Cl. ........................... 604/22; 606/173; 606/180; 606/184
[58] Field of Search ..................... 606/187, 170, 606/173, 184, 171, 180; 604/22; 600/566, 567, 568

[56] References Cited

U.S. PATENT DOCUMENTS

| | | | |
|---|---|---|---|
| 2,710,000 | 6/1955 | Cromer et al. | 128/2 |
| 3,120,845 | 2/1964 | Horner | 128/310 |
| 3,614,953 | 10/1971 | Moss | 128/305 |
| 4,207,874 | 6/1980 | Choy | 128/6 |
| 4,461,305 | 7/1984 | Cibley | 128/754 |
| 4,582,056 | 4/1986 | McCorkle, Jr. | 128/303 R |
| 4,729,763 | 3/1988 | Henrie | 604/22 |
| 4,788,975 | 12/1988 | Shturman et al. | 128/303.1 |
| 5,123,904 | 6/1992 | Shimomura et al. | 604/22 |
| 5,125,924 | 6/1992 | Rudko | 606/12 |
| 5,125,926 | 6/1992 | Rudko et al. | 606/19 |
| 5,133,713 | 7/1992 | Huang et al. | 606/46 |
| 5,242,460 | 9/1993 | Klein et al. | 606/159 |
| 5,336,237 | 8/1994 | Chin et al. | 606/167 |
| 5,358,472 | 10/1994 | Vance et al. | 604/22 |
| 5,358,485 | 10/1994 | Vance et al. | 604/22 |
| 5,380,316 | 1/1995 | Aita et al. | 606/7 |
| 5,383,884 | 1/1995 | Summers | 606/170 |
| 5,389,096 | 2/1995 | Aita et al. | 606/15 |
| 5,403,334 | 4/1995 | Evans et al. | 606/159 |
| 5,429,144 | 7/1995 | Wilk | 128/898 |
| 5,456,689 | 10/1995 | Kresch et al. | 606/180 |
| 5,488,958 | 2/1996 | Topel et al. | 128/754 |

(List continued on next page.)

FOREIGN PATENT DOCUMENTS

| | | | |
|---|---|---|---|
| WO 97/10753 | 3/1997 | WIPO | A61B 17/02 |
| WO 98/05307 | 2/1998 | WIPO | A61K 9/22 |

OTHER PUBLICATIONS

Frazier, O.H., M.D., "Myocardial Revascularization With Laser: Preliminary Findings," *Supplement II Circulation*, vol. 92, No. 9, (Nov. 1995), pp. II–58–II–65.

Hardy, Roger Ian, "A Histologic Study of Laser–Induced Transmyocardial Channels," *Lasers in Surgery and Medicine*, (1987), pp. 6:563–573.

Hershey, John E. et al., "Transmyocardial Puncture Revascularization: A Possible Emergency Adjunct to Arterial Implant Surgery," *Geriatrics*, (Mar. 1969), pp. 101–108.

Kohmoto, Takushi, M.D., "Does Blood Flow Through Holmium: YAG Transmyocardial Laser Channels?," *Ann. Thorac. Surg.*, (1996) pp. 61: 861–868.

Sen, P.K. et al., "Further Studies in Multiple Transmyocardial Acupuncture as a Method of Myocardial Revascularization," *Surgery*, vol. 64, No. 5, (Nov. 1968), pp. 861–870.

White, Manuel et al., "Multiple Transmyocardial Puncture Revascularization in Refractory Ventricular Fibrillation due to Myocardial Ischemia," *The Annals of Thoracic Surgery*, vol. 6, No. 6, (Dec. 1968), pp. 557–563.

*Primary Examiner*—Michael H. Thaler
*Attorney, Agent, or Firm*—Fish & Neave; Nicola A. Pisano

[57] ABSTRACT

Apparatus and methods for intraoperatively performing surgery to create transmural channels in tissue, for example, as in transmyocardial revascularization, are provided using a device including a mechanical end effector and means for stabilizing the end effector in contact with the tissue. The end effector is adapted to cooperate with a source of suction to evacuate tissue severed during the channel forming process, and may optionally include an electrode for cauterizing the tissue surrounding the channel.

36 Claims, 8 Drawing Sheets

U.S. PATENT DOCUMENTS

| | | | |
|---|---|---|---|
| 5,492,119 | 2/1996 | Abrams | 128/642 |
| 5,520,634 | 5/1996 | Fox et al. | 604/22 |
| 5,562,694 | 10/1996 | Sauer et al. | 606/176 |
| 5,569,178 | 10/1996 | Henley | 604/22 |
| 5,569,254 | 10/1996 | Carlson et al. | 606/79 |
| 5,569,284 | 10/1996 | Young et al. | 606/180 |
| 5,575,293 | 11/1996 | Miller et al. | 128/752 |
| 5,575,772 | 11/1996 | Lennox | 604/96 |
| 5,575,787 | 11/1996 | Abela et al. | 606/15 |
| 5,591,159 | 1/1997 | Taheri | 606/15 |
| 5,601,573 | 2/1997 | Fogelberg et al. | 606/143 |
| 5,601,586 | 2/1997 | Fucci et al. | 606/180 |
| 5,601,588 | 2/1997 | Tonomura et al. | 606/185 |
| 5,607,421 | 3/1997 | Jeevanandam et al. | 606/15 |
| 5,609,621 | 3/1997 | Bonner | 607/122 |
| 5,611,803 | 3/1997 | Heaven et al. | 606/114 |
| 5,613,972 | 3/1997 | Lee et al. | 606/107 |
| 5,651,781 | 7/1997 | Grace | 606/1 |
| 5,688,234 | 11/1997 | Frisbie | 604/22 |
| 5,702,412 | 12/1997 | Popov et al. | 606/170 |
| 5,709,697 | 1/1998 | Ratcliff et al. | 606/180 |
| 5,724,975 | 3/1998 | Negus et al. | 128/661.09 |
| 5,743,870 | 4/1998 | Edwards | 604/22 |
| 5,776,092 | 7/1998 | Farin et al. | 604/22 |
| 5,807,401 | 9/1998 | Grieshaber et al. | 606/107 |
| 5,830,222 | 11/1998 | Makower | 606/159 |

APPARATUS FOR PERFORMING TRANSMYOCARDIAL REVASCULARIZATION

This application claims benefit of provisional application Ser. No. 60/032,196 filed Dec. 2, 1996.

FIELD OF THE INVENTION

The present invention relates to apparatus and methods for forming a transmural channel in a hollow-body organ, such as the heart. More particularly, the present invention provides a device that enables a clinician to perform transmyocardial revascularization by mechanically boring channels through the myocardium.

BACKGROUND OF THE INVENTION

A leading cause of death in the United States and the world today is coronary artery disease, in which atherosclerotic plaque causes blockages in the coronary arteries, resulting in ischemia of the heart (i.e., inadequate blood flow to the myocardium). The disease manifests itself as chest pain or angina. In 1996, approximately 7 million people suffered from angina in the United States.

Coronary artery bypass grafting (CABG), in which the patient's chest is surgically opened and an obstructed artery replaced with a native artery harvested elsewhere or a synthetic graft, has been the conventional treatment for coronary artery disease for the last thirty years. Such surgery creates significant trauma to the patient, requires long recuperation times, and poses serious risks of mortality. In addition, experience has shown that the bypass vessel or graft becomes obstructed with time, requiring further surgery.

More recently, catheter-based therapies such as percutaneous transluminal coronary angioplasty (PTCA) and atherectomy have been developed. In PTCA, a mechanical dilatation device is disposed across an obstruction in the patient's artery and then. dilated to compress the plaque lining the artery to restore patency to the vessel. Atherectomy involves using an end effector, such as a mechanical cutting device (or a laser) to cut (or ablate) a passage through the blockage. Such methods have drawbacks, however, ranging from re-blockage of vessels dilated by angioplasty to catastrophic rupture or dissection of the vessel during atherectomy. Moreover, these methods may only be used for that fraction of the patient population where the blockages are few and are easily accessible. Neither technique is suitable for the treatment of diffuse atherosclerosis.

A more recent technique that holds promise of treating a larger percentage of the patient population, including those patients suffering from diffuse atherosclerosis, is referred to as transmyocardial revascularization (TMR). In this method, a series of channels are formed in the left ventricular wall of the heart. These channels may be transmural (i.e., from the epicardium to the endocardium), or only partial (for example, from the endocardium and terminating in the myocardium).

Typically, between 15 and 40 channels about 1 mm in diameter and up to 3.0 cm deep are formed with a laser in the wall of the left ventricle to perfuse the heart muscle with blood coming directly from the inside of the left ventricle, rather than from the coronary arteries. It has also been proposed that the formation of such channels stimulates the creation of small blood vessels within the myocardium. Apparatus and methods have been proposed to create these channels both percutaneously and intraoperatively (i.e., with the chest opened).

U.S. Pat. Nos. 5,380,316 and 5,554,152 to Aita et al. describe intraoperative laser apparatus for forming channels extending from the epicardium to the endocardium. The laser includes an optical wave guide that is held against the patient's heart. several pulses of the laser are required to form a transmural channel by ablation. U.S. Pat. No. 5,389,096 to Aita et al. describes a catheter-based laser system for performing TMR percutaneously, i.e., from within the left ventricle. U.S. Pat. No. 4,658,817 to Hardy describes a laser-based system for intraoperatively performing TMR that includes a needle portion for perforating an outer portion of the tissue, and a laser for ablating the inner portion.

U.S. Pat. No. 5,591,159 to Taheri describes a mechanical catheter-based apparatus for performing TMR involving a catheter having an end effector formed from a plurality of spring-loaded needles. The catheter first is positioned percutaneously within the left ventricle. A plunger is released so that the needles are thrust into the endocardium. The needles are then withdrawn, forming small channels that extend into the myocardium. The patent suggests that the needles may be withdrawn and advanced repeatedly at different locations under fluoroscopic guidance. The patent does not appear to address how tissue is ejected from the needles between the tissue-cutting steps.

The disadvantages of the above-described previously known methods and apparatus for performing TMR are numerous and will impede the acceptance of this new treatment method. For example, laser-based systems, such as described in the Aita et al. patents, require costly and sophisticated laser technology. In addition, the laser apparatus may not provide the clinician sufficient tactile sensation to judge when the endocardium has been punctured, thus creating the risk that laser pulses may be inadvertently directed against other tissue within the left ventricle before the laser is discontinued. Laser-based devices also rely on the clinician to hold the laser element steadily against the beating heart. Moreover, laser-based systems do not provide for removal of ablated tissue, thus causing a risk of embolization by ablated tissue.

Likewise, previously known mechanical systems such as described in the Taheri patent do not address issues such as rebounding of the needle away from the ventricle wall during deployment or how to remove tissue cores from the needles, and again rely on fluoroscopy to determine the location of the distal tip of the device within the heart.

In view of the shortcomings of previously known TMR devices, it would be desirable to provide apparatus and methods for intraoperatively performing surgery, such as TMR, using less costly and more readily available components.

It also would be desirable to provide apparatus and methods for performing TMR that provide the capability to precisely monitor and control the channel forming process, without a risk of inadvertently damaging other tissues within the left ventricle.

It would be desirable to provide apparatus and methods of performing TMR that stabilize an end region of the apparatus against a beating heart.

It further would be desirable to provide apparatus and methods for performing TMR that enable the tissue removed during the channel-forming process to be aspirated, thereby lessening the potential for embolization.

SUMMARY OF THE INVENTION

In view of the foregoing, it is an object of this invention to provide apparatus and methods for intraoperatively performing surgery, such as TMR, using less costly and more readily available components.

It is another object of this invention to provide apparatus and methods for performing TMR that provide the capability to precisely monitor and control the channel forming process, without a risk of inadvertently damaging other tissues within the left ventricle.

It is a further object of the present invention to provide apparatus and methods of performing TMR that stabilize an end region of the apparatus against a beating heart.

It is also an object of the present invention to provide apparatus and methods for performing TMR that enable the tissue removed during the channel-forming process to be aspirated, thereby lessening the potential for embolization.

These and other objects of the present invention are accomplished by providing apparatus and methods for intraoperatively performing TMR with a device including an end region having a mechanical cutting head for forming transmural channels and means for stabilizing the end region in contact with the beating heart. The cutting head is adapted to cooperate with a source of suction to evacuate tissue severed during the channel-forming process, and may optionally include an electrode for cauterizing the tissue surrounding the channel.

In one preferred embodiment of the apparatus of the present invention, the mechanical cutting head comprises a rotating tubular element having a central lumen through which severed tissue is aspirated, while the means for stabilizing the end region in contact with the tissue comprises a suction cup. In alternative embodiments the cutting head may be arranged for longitudinal motion, a combination of angular and longitudinal motion, or vibratory motion. The stabilizing means may alternatively comprise an element that pinches or retractably impales the epicardium. The shaft carrying the end region may be either straight or angled, to access posterior regions of the left ventricle.

Methods of using the apparatus of the present invention to perform surgery, such as transmyocardial revascularization, are also provided.

BRIEF DESCRIPTION OF THE DRAWINGS

Further features of the invention, its nature and various advantages will be more apparent from the accompanying drawings and the following detailed description of the preferred embodiments, in which:

FIGS. 17A to 17C are sectional and perspective views of various embodiments of stabilizing means for holding the end region of the present invention in contact with a beating heart, while

DETAILED DESCRIPTION OF THE INVENTION

The present invention relates generally to apparatus and methods for performing surgery involving forming a channel in a hollow-body organ, and more particularly, for intraoperatively performing transmyocardial revascularization. Unlike previously known laser apparatus developed for TMR, the present invention may be implemented using relatively low cost mechanical and electrical components.

Figure 1:
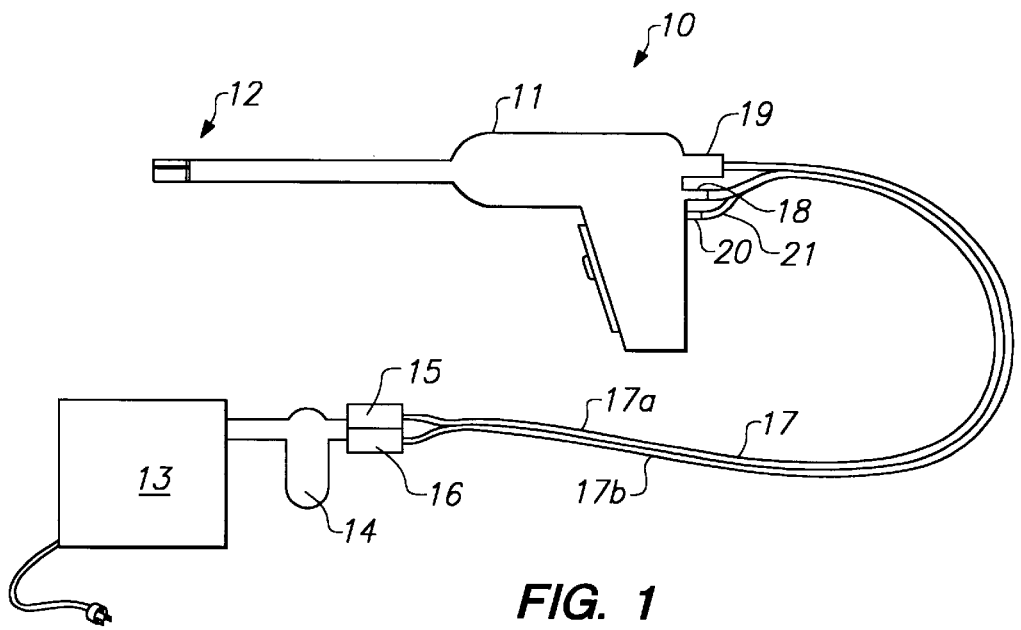
FIG. 1 is a perspective view of an illustrative embodiment of apparatus constructed in accordance with the present invention.

Referring to FIG. 1, illustrative apparatus 10 constructed in accordance with the present invention is described. Apparatus 10 includes hand-held device 11 including end region 12 for forming channels in the heart, vacuum source 13 including collection trap 14 and valves 15 and 16. Device 11 is coupled to vacuum source 13 via multi-lumen flexible hose 17.

Vacuum source 13, collection trap 14 and valves 15 and 16 each may be previously known devices. For example, vacuum source 13 may be a conventional medical vacuum source that provides a high level of suction, e.g., between about 400–800 mm Hg, and preferably about 730 mm Hg. Vacuum source 13 includes trap 14 for collecting material aspirated through flexible hose 17. In accordance with the present invention, vacuum source 13 includes two valves upstream of the collection trap which provide different levels of suction for specific purposes. Valve 15 reduces the high level suction created by vacuum source 13 to a lower level, e.g., less than 400 mm Hg and preferably, about 250 mm Hg, and may be selectively opened to provide a low level suction to lumen 17a of hose 17. Valve 16 is configured to be selectively opened to provide the high level suction to lumen 17b of hose 17 to aspirate material severed by the cutting head.

This description of the invention is organized as follows: the components of an illustrative embodiment are first described, a description of operation of the device is provided, and alternative embodiments and optional components are then described. As will be understood from the following description, specific components of the device may be interchanged with functionally equivalent components of the alternative embodiments set forth hereinafter to achieve the goals of the present invention.

Figure 2:
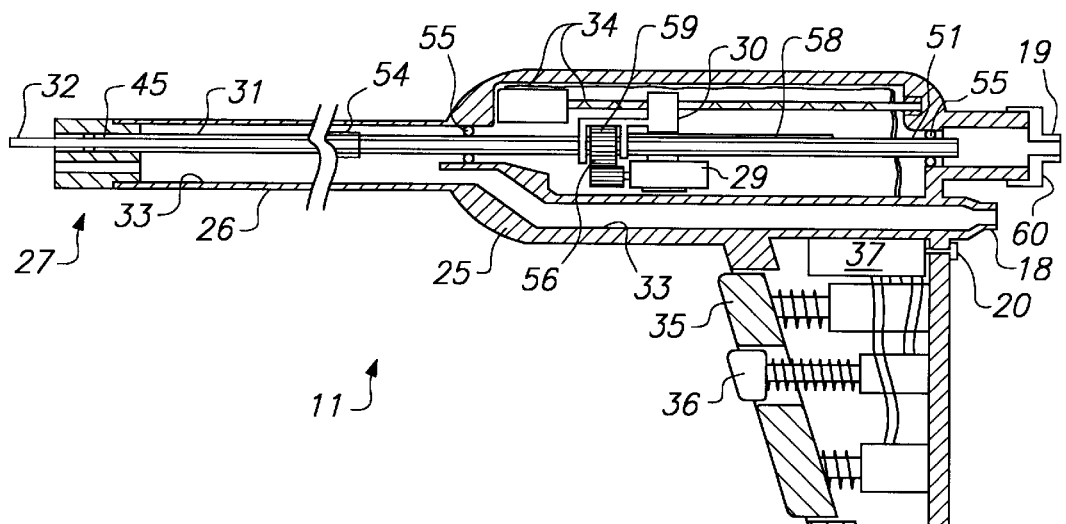
FIG. 2 is a cross-sectional elevation view of the device of FIG. 1.

Referring to FIG. 2, an illustrative embodiment of device 11 of the present invention is described. Device 11 includes housing 25 having shaft 26, stabilizing means 27 disposed on the distal end of shaft 26, motor 29 affixed to cradle 30, drive tube 31 coupled to motor 29 and having cutting head 32 disposed on the distal end of drive tube 31, linear actuator mechanism 34 coupled to cradle 30, and switches 35 and 36 coupled to control circuitry 37. Lumen 17a of hose 17 couples valve 15 to port 18 of device 11, while lumen 17b couples valve 16 to port 19. Control signals and electrical power are supplied to device 11 and valves 15 and 16 via electrical connector 20 and lead wires 121 affixed to hose 17.

In accordance with the present invention, a clinician actuates switch 35 to activate valve 15. Valve 15, in turn, opens to provide low level suction through lumen 33 to stabilizing means 27. Activation of switch 35 also causes motor 29 to rotate drive tube 31 at high speed. The clinician then contacts stabilization means 27 to a portion of the patient's anatomy, e.g., the epicardium over the left ventricle, so that the stabilization means engages the tissue. The clinician then actuates switch 36, which causes control circuitry 37 to actuate linear actuator mechanism 34 to extend and retract cutting head 32, thereby forming a channel in the tissue. It has been observed that the outlet of such a channel will clot off in a few minutes, leaving a channel through which blood from the left ventricle may perfuse the myocardium. Switch 35 is then actuated again to disengage stabilization means 27 from the tissue. The device is then repositioned, and the procedure repeated to create additional transmural channels.

Figure 3A:
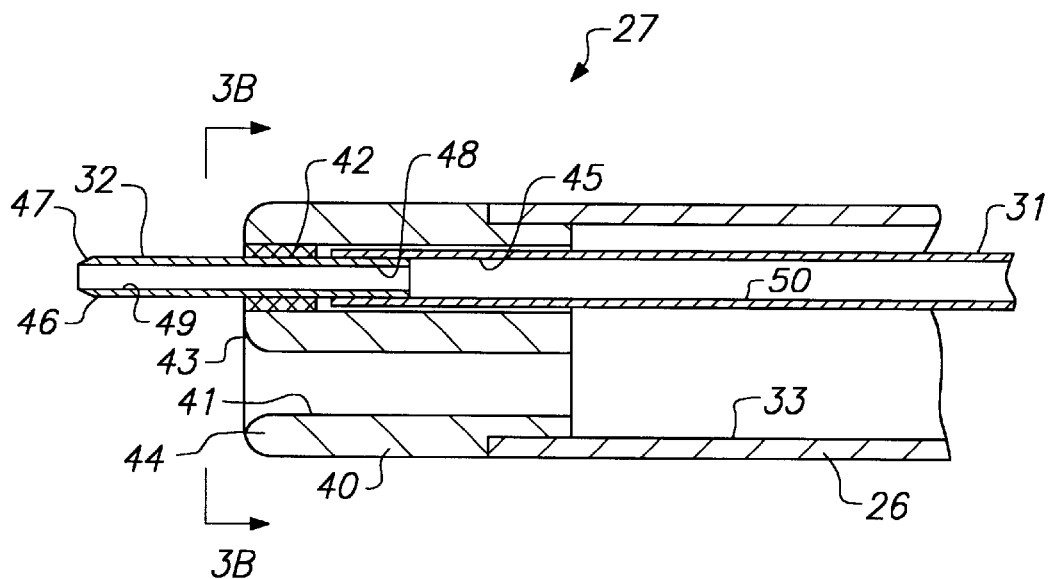
FIGS. 3A and 3B are, respectively, a partial side cross-sectional view and an end view of the end region of the device of FIG. 2.
Figure 3B:
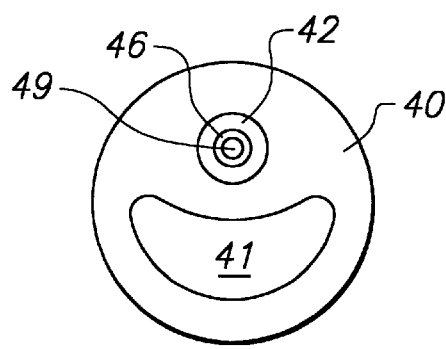

Referring now to FIGS. 2, 3A and 3B, illustrative embodiments of stabilization means 27 and cutting head 32 of the present invention are described. In FIGS. 2 and 3A, cutting head 32 is shown fully extended. Stabilization means 27 comprises suction cup 40 having opening 41 that communicates through lumen 33 of shaft 26, and hose 17, with vacuum source 13. Valve 15 reduces the high level of suction provided by vacuum source 13 to a lower level, e.g. less than 400 mm Hg, so that hematomas do not form where suction cup 40 engages the tissue.

Suction cup 40 preferably comprises a transparent material, such as silicone, polyurethane, polyethylene, polypropylene or polycarbonate, so that the path of cutting head 32 is visible. Stabilization means 27 includes bushing 42 comprising a low frictional material, e.g., polytetrafluoroethylene (teflon), that supports cutting head 32. In some embodiments of device 11, bushing 42 also may act as a stop for forward displacement of the drive tube and cutting head. Bushing 42 provides a bearing surface for both rotational and reciprocatory motion of cutting head 32. Distal end face 43 of suction cup 40 may optionally include a traumatic profile 44 (i.e., rounded edges) so as to further reduce the risk of injury to the tissue at points of contact.

Cutting head 32 comprises tubular member 46 formed from a rigid biocompatible material, such as stainless steel, and includes sharpened distal end 47 and proximal end 48 engaged in distal end 45 of drive tube 31. Tubular member 46 includes central lumen 49 through which severed tissue is drawn by high pressure suction applied at the proximal end of drive tube 31 through lumen 50. Tubular member 46 preferably has a wall thickness of 0.002 to 0.005 inches, and a length sufficient to pass completely through the tissue wall when fully extended by linear actuator mechanism 34, as described hereinbelow.

In accordance with the methods of the present invention, cutting head 32 is rotated at high speeds, e.g., 500 to 50,000 RPM, to achieve a number of important advantages, including: reduced drag on the tissue during penetration; enhanced cutting with cleaner edges; at higher RPM, the friction caused by the cutting head rotating against the tissue causes some coagulation; and reduced risk that severed tissue will be ejected, lowing the risk of embolization by such tissue. In addition, the distal end face of the cutting head may be flat or serrated, and may be electrically conductive to form an active electrode, for example, when connected to an RF generator in a monopolar arrangement, for coagulating the tissue defining the transmural channel.

Cutting head 32 also may include an internal taper or internal threads (see FIG. 13B), to assist in aspirating lumen 49, and also may be coated with a lubricious material, inside and out. Alternatively, if it is desired to partially coagulate the tissue defining the transmural channel with friction-generated heat, it may be desirable to coat the exterior of the cutting head with titanium dioxide or diamond grit, or to sand blast the exterior surface of the cutting head to provide a rougher texture.

Drive tube 31 includes lumen 50, extending from distal end 45 to proximal end 51, through which tissue severed by cutting head 32 is aspirated by a high level vacuum from vacuum source 13. Drive tube 31 transmits rotational motion, imparted by motor 29 through drive tube 31 to cutting head 32 at a predetermined speed, e.g., 500 to 50,000 RPM. In one preferred embodiment, motor 29 is an electric motor having a stall torque of between about 0.5 and 10 oz-inch, and is sufficiently compact (e.g., having a length 1–3 inches and a diameter of 0.5–1.0 inches) to fit within housing 25. Alternatively, motor 29 may be replaced with a pneumatic motor, air-driven turbine, hydraulic motor, or an external unit that is coupled to device 11 by a cable.

Figure 4:
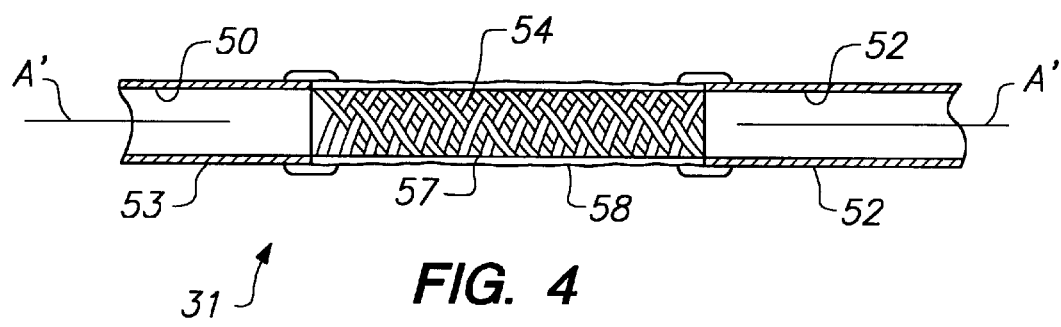
FIG. 4 is a partial side sectional view of the drive tube of the present invention.

Referring to FIG. 4, drive tube 31 comprises rigid proximal portion 52 and distal portion 53 coupled by flexible drive coupling 54. Central lumen 50 extends through each of portions 52–54. Rigid proximal portion 52 of drive tube 31 is disposed in housing 25 on O-rings 55 and is coupled to motor 29 by gear ring 56. Cutting head 32 is coupled to distal end 45 of rigid distal portion 53 as described hereinabove. Drive coupling 54 comprises, for example, tube 57 formed of braided stainless steel wire having a teflon coating 58. Drive coupling 54 is capable of transmitting rotational and linear motion while subjected to slight lateral deflection. Thus, drive coupling 54 transmits motion from rigid proximal portion 52 to rigid distal portion 53 even though longitudinal axis A of proximal portion 52 is not in complete alignment with longitudinal axis A' of distal portion 53.

In accordance with one aspect of the present invention, drive tube 31 and cutting head 32 preferably are intended for single patient use, and are therefore removable, while the remainder of device 11 is sterilizable for repeated use. In accordance with this scheme, gear ring 56 slides along key 58 projecting from the exterior surface of proximal region 52 of drive tube 31. Fork 59 keeps gear ring 56 aligned with the pinion gear of motor 29, while causing gear ring 56 to slide along key 58 of the drive tube. Locking cap 60 may be removed, e.g., unthreaded, from the back of housing 25, and drive tube 31 may be retracted proximally for replacement with a new drive tube and cutting head.

In addition, any of a number of similar seals or bearings may be substituted for O-rings 55, e.g., lip seals, sleeve bearings, spring energized bushings, or O-rings having a multi-lobe cross-section, such as the Quad Ring®, a registered trademark of Pacific Rubber Company, San Carlos, Calif.

Figure 5:
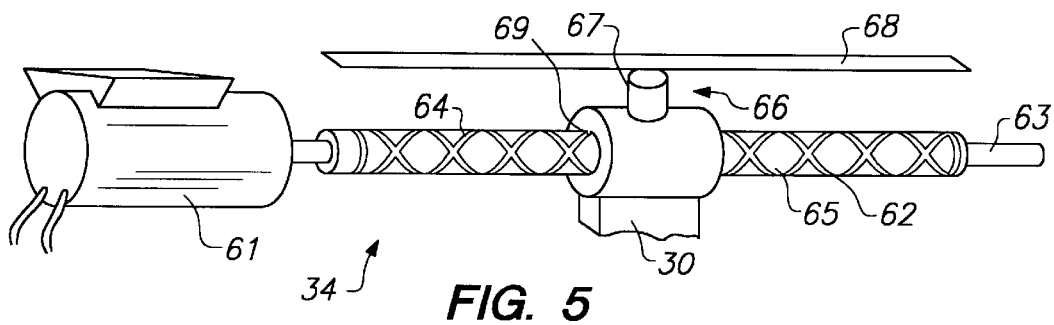
FIG. 5 is a partial perspective view of an illustrative linear actuator mechanism suitable for use in the device of the present invention.

Referring now to FIG. 5, linear actuator mechanism 34 of the embodiment of FIG. 2 is described. This mechanism extends and retracts cutting head 32 responsive to commands received from control circuitry 37 and switch 36. Linear actuator 34 comprises motor 61 coupled to double-action lead screw 62 at one end and bushing 63 at the other end. Carriage 30, which supports motor 29 coupled to drive tube 31, is disposed on lead screw 62 so that tooth 69 of carriage 30 glides in grooves 64, 65 of the lead screw. Lead screw includes groove 64 that urges carriage 30 along the lead screw in a distal direction, while groove 65 urges carriage 30 along the lead screw in a proximal direction. Grooves 64 and 65 interconnect at the proximal and distal ends of the lead screw, so that when motor 61 rotates the lead screw a predetermined number of turns, the carriage is first extended distally and then retracted proximally.

Figure 6:
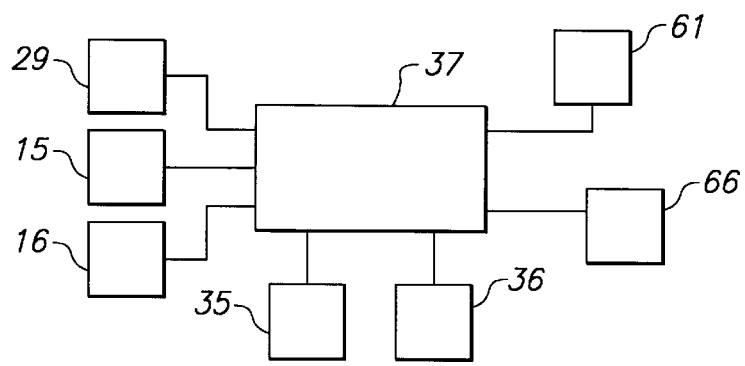
FIG. 6 is a block diagram depicting the electrical components and connections of the device of FIG. 1.

Carriage 30 preferably also includes position sensing element 66 that indicates the displacement of carriage 30, and hence, the extension of cutting head 32. This positional information may be fed back to control circuitry 37 to form a closed loop system, in which motor 61 can be controlled to extend and retract cutting head 32 with a preselected velocity profile. In FIG. 6, position sensing element 66 illustratively comprises a potentiometer having electrical contact 67 disposed on carriage 30 and strip contact 68 affixed to an interior surface of housing 25. Strip contact 68 preferably has a uniform resistivity along its length, so that the resistance encountered by a low voltage current applied between contacts 67 and 68 may be correlated to displacement of the carriage.

As will be readily apparent, other mechanisms may be advantageously substituted for linear actuator mechanism 34 and position sensing element 66 in the above-described embodiment. For example, linear actuator mechanism 34 may comprise an air cylinder, a lead screw driven by an external motor via cable, or a hydraulic cylinder, and may be open-circuit or servo-controlled. Motor 61 may be electric, pneumatic or hydraulic. Linear actuator mechanism 34 may even be replaced with a manually operated structure, as described hereinbelow with respect to FIGS. 12 and 13.

Likewise, the potentiometer of the foregoing embodiment may be replaced with functionally equivalent structure, such as a linearly variable displacement transducer (LVDT), differential transformer, linear or rotary optical encoder, or capacitance or magnetic based displacement measuring systems. Each of these displacement measuring systems may be used to determine relative or absolute displacement of carriage 30, to provide instantaneous position information to control circuitry 37.

Referring now to FIG. 6, control circuitry 37 is described. Control circuitry 37 may be either analog or digital, and if the latter, may be a collection of components, an application specific integrated circuit, or a suitably programmed general purpose microprocessor. Control circuitry 37 is electrically coupled to switches 35 and 36, motors 29 and 61, and vacuum control valves 15 and 16. Control circuitry 37 preferably is programmed to control the application of low and high level vacuum to stabilization means 27 and cutting head 32, respectively, and to control the speeds of motors 29 and 61.

More particularly, control circuitry 37 is programmed to actuate valve 15 that connects suction cup 40 to vacuum source 13, thereby providing a low level of suction through suction cup 40 when switch 35 is depressed. Simultaneously, control circuitry 37 energizes motor 29 to begin rotating drive tube 31. The clinician then contacts the distal end of device 11 to the tissue in which the channel is to be formed, and suction cup 40 engages and stabilizes the distal end of device 11 against the tissue, e.g., the beating heart.

At a predetermined moment, e.g., at a predetermined point in the cardiac cycle, the clinician actuates switch 36, thereby causing control circuitry 37 to energize motor 61. Control circuitry 37 also opens valve 16 to connect lumen 49 of cutting head 32 to high level vacuum induced by vacuum source 13 via lumen 50. As motor 61 rotates, it causes carriage 30 to be advanced and then retracted along the length of lead screw 62, thereby extending and retracting cutting head 32. The high level vacuum drawn through lumen 50 of drive tube 31 and lumen 49 of cutting head 32 aspirates the severed material from the operative site and into collection trap 14 of vacuum source 13. The clinician then redepresses, or releases, switch 35 to cause control circuitry 37 to close valve 15, thereby terminating low level suction through the suction cup and permitting the distal end of device 11 to be repositioned to form another transmural channel.

Figures 7A, 7B, 7C, 7D, 7E:
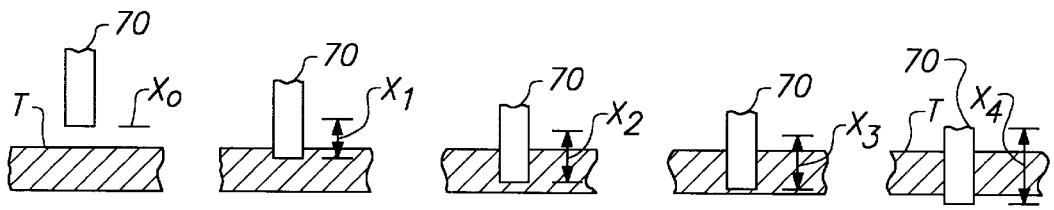
FIGS. 7A to 7E and 7F are, respectively, side views of the cutting head of FIG. 2 as it penetrates a thickness of tissue, and a graph showing the linear speed of the cutting head as a function of displacement.
Figure 7F:
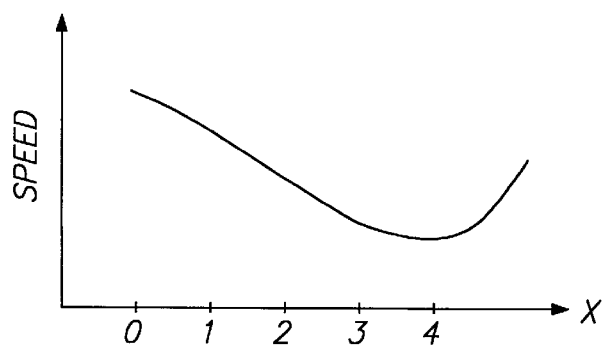

Referring now to FIGS. 7A to 7F, a speed control feature of a preferred embodiment of the present invention is described. In FIGS. 7A to 7E, the position of cutting head 70 at a series of consecutive displacements $X_0$–$X_4$ is shown during the process of forming a transmural channel in tissue T. FIG. 7F depicts the speed of the cutting head at each of the displacements illustrated in FIGS. 7A to 7E.

In accordance with the present invention, the linear speed of cutting head 32 varies in accordance with the depth of penetration of the cutting head into tissue T. As shown in FIGS. 7C and 7D, as the cutting head nears the inner surface of the tissue wall (near completion of the channel formation), the speed of the cutting head is reduced to provide adequate time for the high level suction to aspirate severed material. In this manner, the potential for ejecting severed material into the organ from the distal surface of the tissue is reduced, and thus the risk of embolization is reduced. After the cutting head has completely penetrated the tissue wall, the cutting head, is rapidly retracted.

In a preferred embodiment of device 11, control circuitry 37 may be programmed to control the speed at which motor 61 drives lead screw 62 to provide a speed profile such as described above with respect to FIG. 7F. If motor 61 is a constant speed motor, lead screw 62 may alternatively have a variable pitch thread to vary the extension and retraction speed of the cutting head. Control circuitry 37 may in addition employ positional information generated by position sensing element 66 to more accurately control the speed profile. In addition, control circuitry may also employ a signal generated by a pressure monitor connected to the high level suction lumen to determine when the cutting head has completely penetrated the tissue, as described hereinafter in connection with FIG. 14.

Figure 8A:
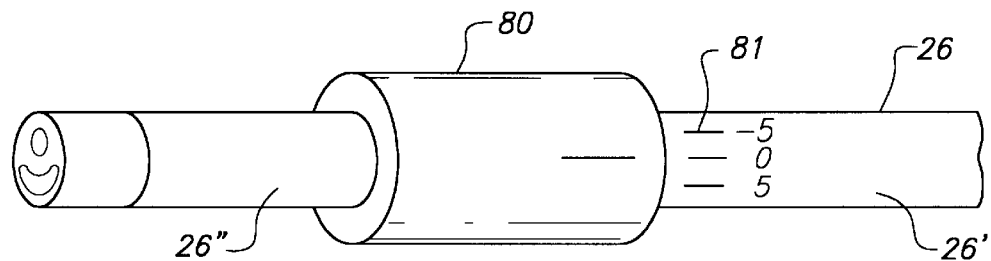
FIGS. 8A to 8C are, respectively, a partial perspective view and side sectional views of an adjustable length shaft suitable for use in the device of FIG. 2.
Figure 8B:
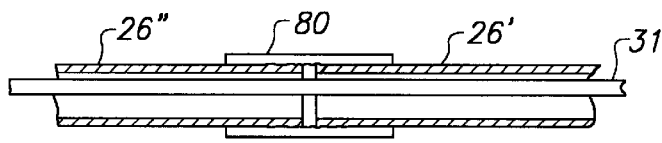
Figure 8C:
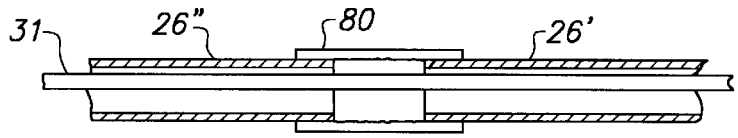

With respect to FIGS. 8A to 8C, an embodiment of the apparatus of FIG. 1 is described wherein the shaft 26 includes collar 80 that may be rotated to lengthen or shorten the length of the shaft. More specifically, the distal region of shaft 26 comprises pieces 26' and 26" which are engaged via opposingly-handed threads in collar 80. Thus, when collar 80 is rotated in one direction, the overall length of shaft 26 increases a corresponding amount (see FIG. 8B), while rotation of the shaft in the opposite direction shortens the overall length of shaft 26 (see FIG. 8C). Shaft piece 26' may include fiducial marks 31 to indicate the distance by which the overall shaft length is shortened or lengthened.

Because the length of drive tube 31 is uneffected by movement of collar 80, the maximum extension of cutting head 32 beyond the distal end face of suction cup 40 may be adjusted using collar 80. The embodiment of FIG. 8A therefore provides a mechanism for controlling the maximum depth which the cutting head can achieve in response to actuation of linear actuation mechanism 34.

Figure 9A:
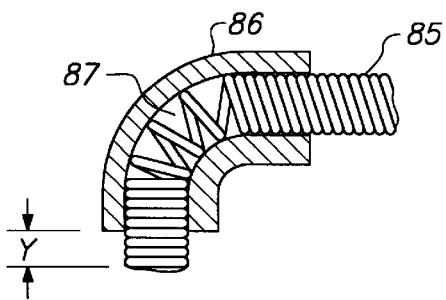
FIGS. 9A and 9B are side views of a drive tube and sleeve capable of driving a cutting head in an angled shaft.
Figure 9B:
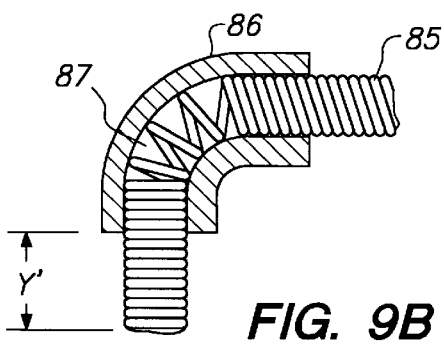

Referring now to FIGS. 9A and 9B, components are described for use in an embodiment of the apparatus of FIG. 2 suitable for forming channels in the posterior surface of the left ventricle. For such an application, it may be necessary to bend the cutting head through an angle of 90° with respect to the longitudinal axis of the drive tube.

In FIG. 9A, rigid distal portion 53 of the drive tube of FIG. 4 is replaced by closely wound coil spring 85. Coil spring 85 is comprised of a resilient and elastic material, such as a plastic or metal alloy, so that adjacent turns of the coil form a nearly pressure-tight seal when the spring is undeformed. Coil spring 85 may include a coating of a lubricious material, e.g., a sputtered coating of polytetrafluoroethylene (teflon). Sleeve 86 is provided to create a 90° bend in coil spring 85 and forms a nearly pressure-tight seal with coil spring 85 where the spring enters and leaves the sleeve. Sleeve 86 preferably comprises a plastic material, e.g., Delrin®, a registered trademark of E.I. Dupont de Nemours company, Wilmington, Del., for polyacetal compounds, or polyethylene. Within sleeve 86, gaps 87 form between adjacent turns of the bent portion of the spring, but it is expected that sleeve 86 will maintain a high level of suction through coil spring 85 without leakage sufficient to adversely impact the ability of the vacuum source to aspirate material severed by cutting head 32.

As illustrated in FIG. 9A, coil spring 85 (which carries the cutting head) extends beyond the distal edge of sleeve 86 by an initial distance Y. Upon actuation of linear actuation mechanism 34, the drive tube urges coil spring 85 and the attached cutting head (not shown) in the distal direction. As the coil exits through the distal opening in sleeve 86, the adjacent turns of the coil spring close together, thus preserving the high level vacuum, while gaps 87 form between the turns of the coil spring entering through the proximal opening of sleeve 86. As noted above, however, sleeve 86 functions to retain the high level suction through the coil spring, without significant degradation. Thus, as depicted in FIG. 9B, the linear actuation mechanism and drive tube may extend coil spring 85 (and cutting head 32) to a extended displacement Y' while rotating the cutting head and providing adequate high level suction to aspirate severed tissue.

Figure 10:
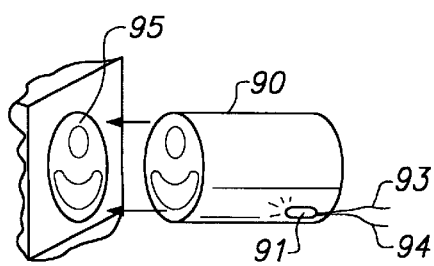
FIG. 10 is a partial perspective view of an alternative embodiment of the stabilization means of FIG. 2.

With respect to FIG. 10, an alternative embodiment of the stabilization means of the present invention is described. Suction cup 90 includes a light emitting diode (LED) or a laser diode 91 disposed in the transparent material forming the suction cup, and which is connected to a power supply by lead wires 93 and 94. When a voltage is supplied across lead wires 93 and 94, LED 91 emits light that exits the distal end face of the suction cup in the form of an approximately annular illumination beam to form illuminated image 95. Applicant expects that this annular illumination beam may be advantageously used to position the distal end of device 11 on the tissue so that the suction cup area does not overlap a site at which a transmural channel had been previously formed. Alternatively, shaft 26 may include a spring-loaded retractable stylet (not shown) that indicates the position of the suction cup before the suction cup is engaged to the tissue.

Figure 11A:
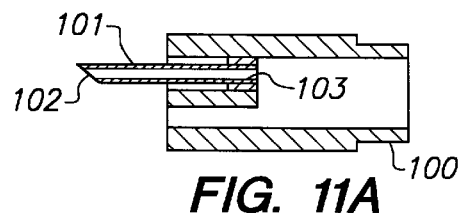
FIGS. 11A and 11B are side sectional views of further alternative embodiments of the stabilization means of FIG. 2.

Referring now to FIGS. 11A and 11E, further alternative embodiments of stabilization means constructed in accordance with the present invention are described. In FIG. 11A, suction cup 10C is similar in design to that of FIG. 3A, except that bushing 42 is replaced by tube 101 having beveled sharpened tip 102 and lumen 103. The bevel of tip 102 renders the tip non-coring, so that when the beveled end of tube 101 is inserted into the tissue, a flap of tissue is cut and folded back, rather than severed. Cutting head 32 is reciprocated through lumen 103 of suction cup 100 as described hereinabove. Applicant expects that use of beveled tube 101 will accelerate the process of clotting of the channel on the epicardium, by reducing the amount of tissue removed from outer thickness of the tissue wall, and leaving a slit instead of a cored cut channel at the surface.

Figure 11B:
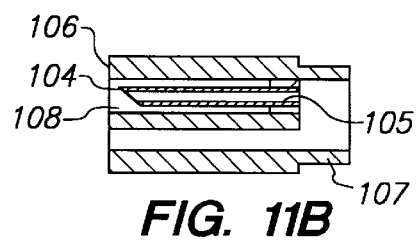

In FIG. 11B, an alternative embodiment of the suction cup of FIG. 11A is shown, in which beveled tip 104 of tube 105 is disposed flush with, or slightly recessed from, distal end face 106 of suction cup 107. In this embodiment, beveled tip 104 of the suction cup does not pierce the surface of the tissue until the high level suction draws the tissue inwards through opening 108 of suction cup 107. It is expected that the embodiment of FIG. 11B will provide the same advantage as the embodiment of FIG. 11A, i.e., less outer wall tissue removal and faster hemostasis, but with a lower risk of inadvertently piercing or tearing the tissue while repositioning the distal end of the device.

Figure 12:
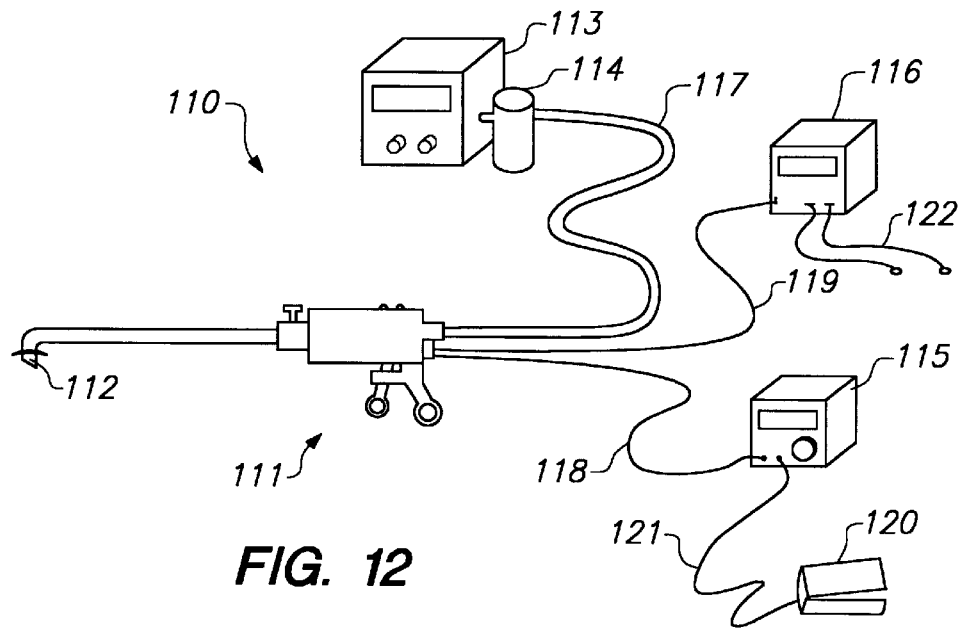
FIG. 12 is a perspective view of an alternative embodiment of the apparatus of the present invention.

Referring now to FIG. 12, an alternative embodiment of apparatus constructed in accordance with the present invention is described. Apparatus 110 includes hand-held device 111 including end effector 112 for forming channels in the heart, vacuum source 113 including collection trap 114, RF energy source 115, and optional EKG monitor 116. Device 111 is coupled to vacuum source 113 via flexible hose 117, and to RF energy source 115 and EKG monitor 116 via lead wires 118 and 119, respectively. RF energy source 115 is selectively activated by footpedal switch 120, connected to RF energy source 115 by cable 121.

Vacuum source 113, RF energy source 115 and EKG monitor 116 may be previously known devices. For example, vacuum source may be a conventional medical vacuum source and includes trap 114 for collecting material aspirated through flexible hose 117. RF energy source 115 may be of the type widely used in monopolar and bipolar electrosurgery, for example, the Valleylab Force 2, sold by Valleylab, Inc., Boulder, Colo. Optional EKG monitor 116 includes leads 122 for monitoring cardiac activity and generating an output corresponding thereto.

Figure 13A:
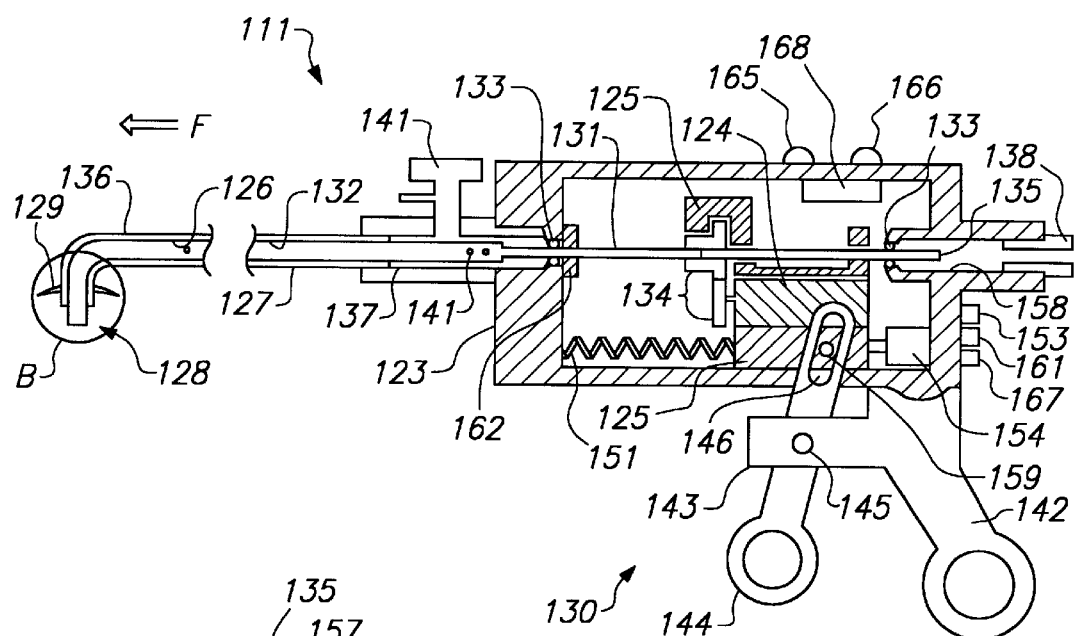
FIGS. 13A and 13B are, respectively, a cross-sectional elevation view and a detailed cross-sectional view of the distal end of the apparatus of FIG. 12.
Figure 13B:
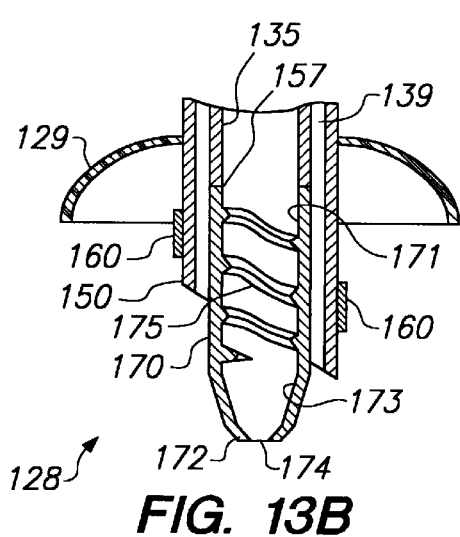

Referring now to FIGS. 13A and 13B, , device 11 includes housing 123, motor 124 carried in cradle 125, drive tube 126 disposed in shaft 127, cutting head 128, suction cup 129 and handle assembly 130.

Drive tube 126 comprises rigid proximal portion 131 and flexible distal portion 132. Rigid proximal portion 131 is disposed in housing 123 on O-rings 133 and is coupled to motor 124 by gearing 134. Flexible distal portion 132 extends through shaft 127 to distal end 157, where it terminates in cutting head 128. Shaft 127 may include bend region 136 enabling access by cutting head 128 to posterior portions of the heart, or may alternatively comprise a flexible material that can be bent to a desired shape and retains that shape. Rigid proximal portion 131 preferably comprises a metal alloy (e.g., stainless steel), while flexible distal portion 132 comprises, for example, a plastic or elastomer reinforced mesh or coil, such as sold by Adam Spence Company, Wall, N.J. Housing 123 preferably comprises a sturdy metal alloy or plastic.

Drive tube 126 is slidably disposed within shaft 127 so that the drive tube may rotate or vibrate, while shaft 127 is fixed to housing 123. Proximal end 135 of rigid proximal portion 131 is disposed in passage 158 that communicates with flexible tubing 117 via luer 138. Rigid proximal portion 131 is coupled to motor 124 by gearing 134, which preferably has a gear ratio in a range of 2:1 and 10:1. In the illustrative embodiment of FIGS. 13, motor 124 and gearing 134 cause drive tube 126 to rotate at speeds in a range of 500 to 50,000 rpm, and more preferably, about 8000 rpm.

A clearance is provided between drive tube 126 and shaft 127 to define annular gap 139. Annular gap 139 allows suction to be drawn through suction cup 129. Suction is induced in cavity 137 by holes 140 in drive tube 126 that communicate with cavity 1L37. Trumpet valve 141 is disposed on housing 123 in communication with cavity 137, so that valve 141 may be depressed to break the suction drawn through suction cup 129.

Housing 123 includes a portion defining fixed handle member 142 and yoke 143. Movable handle member 144 pivots within yoke 143 on pin 145, and includes slot 146 near its upper end. Pin 159 is affixed to cradle 125 and rides in slot 146 of movable handle member 144, so that when movable handle member 144 is compressed toward fixed handle member 142, cradle 125 and drive tube 126 slide in the distal direction (indicated by arrow F). Distal movement of drive tube 126 causes cutting head 128 to extend from distal end 150 of shaft 127. When the compressive force on handle member 144 is released, spring 151 pushes cradle 125 in the proximal direction, returning the cradle to its starting position.

Distal end 150 of shaft 127 forms a punch having a sharpened edge that forms a semi-circular slit in the outer surface of the tissue, when suction cup 129 is actuated to engage the heart. The semi-circular shape of the entry wound formed by the sharpened edge is expected to aid in closure of the wound subsequent to withdrawal of cutting head 128, as described above with respect to FIGS. 11A and 11B.

Motor 124 is coupled to a power supply via plug 153 on housing 123. Housing 123 also contains motion switch 154 that controls operation of motor 124. In particular, spring 151 biases cradle 125 against motion switch 154 so that the switch and motor are off. When the clinician compresses handle member 144 towards handle member 142, cradle 125 moves away fro m. motion switch 154, thereby activating switch 154 to turn motor 124 on. When the compressive force on hand member 144 is relaxed and spring 151 returns cradle 125 to its proximal-most position, motion switch 154 is again depressed, shutting motor 124 off.

Device 111 includes electrode 160 disposed on shaft 127 adjacent distal end 150 (see FIG. 13B), while cutting head 128 comprises either an active electrode of a monopolar arrangement or one electrode of a bipolar arrangement. Electrode 160 and cutting head 128 are coupled to RF energy source 115 (via drive tube 126) via plug 161, bushing 162 and lead wires (not shown) connecting plug 161 to bushing 162 and electrode 160. Drive tube 126 therefore preferably includes a thin layer of electrical insulation (e.g., polyimide shrink tubing) over those regions that contact shaft 127, to electrically isolate drive tube 126 from the shaft. Application of RF energy to cutting head 128 and electrode 160 is controlled by operation of footpedal switch 120.

Housing 123 may optionally include red light 165 and green light 166 that are coupled to EKG monitor 116 via plug 167. In accordance with one aspect of the present invention, applicant expects that it may be desirable to form channels in the heart muscle only during diastole, when the heart muscle is relaxed. In this manner, applicant expects that difficulties created during movement of the heart associated with systole may be avoided. Accordingly, EKG monitor 116 may be provided to monitor cardiac activity, and outputs a signal corresponding to contraction and relaxation of the heart. The output of EKG monitor is processed via logic 168 which determines the onset of diastole, and illuminates green light 166, thereby informing the clinician that the handle assembly may be actuated. Likewise, when logic 168 determines the onset of systole, red light 165 is illuminated, thereby informing the clinician to wait.

Referring to FIG. 13B, end effector 112 of device 111 of FIG. 13A is shown in greater detail. End effector 112 comprises cutting head 128 including tubular member 170 having central lumen 171 and sharp beveled distal end 172. In a preferred embodiment, cutting head 128 has frustoconical region 173 including aperture 174 that preferably is 30% or more smaller than the diameter of central lumen 171. Applicant expects that by providing a larger diameter for central lumen 171 than aperture 174, the potential for severed tissue to become lodged in central lumen 171 is reduced.

Cutting head 128 preferably includes raised threads 175 projecting within central lumen 171 that push severed tissue in the proximal direction. The interior of central lumen 171 also may be coated with a lubricious material, such as polytetrafluoroethylene, that reduces sticking of tissue to the interior of central lumen 171.

Cutting head 128 is coupled to drive tube 126, by suitable means (e.g., threads or welding) and is rotated at high speeds by motor 124 and gearing 134. When extended in the distal direction by actuation of handle assembly 130, cutting head 128 is capable of boring a channel in tissue, such as heart muscle. Cutting head 128 preferably comprises an electrically conductive material capable of retaining a sharp edge, such as, such as stainless steel type 303, 304 or hardened tool steel, and is electrically coupled to drive tube 126. In this manner, cutting head 128 permits RF energy to be conducted to the tissue forming the channel, thereby coagulating the tissue.

Alternatively, beveled surfaces 172 of the cutting head 128 may be treated to provide a high-friction surface finish. As described hereinabove, it is expected that high speed rotation of drive tube 126 and cutting head 128 will cause sufficient frictional heating of the tissue surrounding the channel bored by the cutting head to cause coagulation of the tissue. In this case RF energy source 115 and the related hardware components may be omitted, thereby simplifying the design and reducing the cost of the apparatus.

Figure 14:
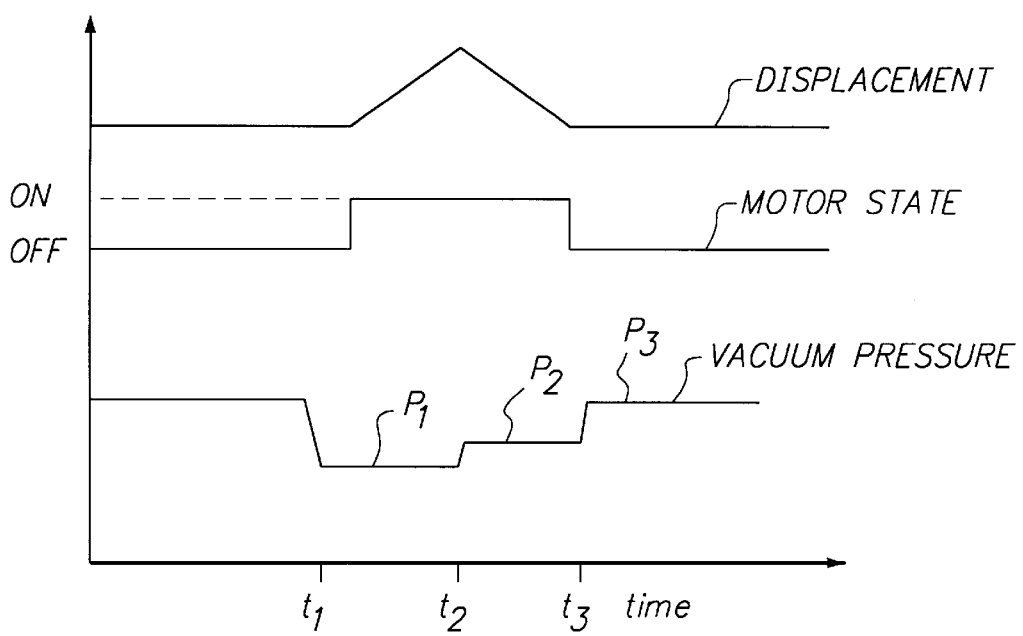
FIG. 14 is a diagram illustrating events occurring during operation of the device of FIG. 12.

Referring now to FIG. 14, operation of apparatus 110 in accordance with the methods of the present invention is described. In accordance with known surgical methods for performing TMR, a portion of the patient's left ventricle is exposed by thoracotomy or through apertures opened between the patient's ribs. The clinician then brings the distal portion of device 111 into contact with the epicardium in the vicinity of the left ventricle, so that suction drawn through suction cup 129 causes the suction cup to engage the heart. Engagement of suction cup 129 with the epicardium is accompanied by a decrease in pressure through suction cup 129, as indicated by pressure $P_1$ occurring at time $t_1$ in FIG. 14. During this engagement, sharpened distal end 150 of shaft 127 creates a semi-circular incision in the epicardium.

The clinician then compresses handle assembly 130 to move cradle 125 away from motion switch 154, thereby activating motor 124 to cause cutting head 128 to begin rotating. If provided, clinician may await illumination of green light 166, responsive to signals provided from EKG monitor 116, before fully compressing handle assembly 130. As handle assembly 130 is compressed further, cutting head 128 passes through the entry wound created by sharpened distal end 150, and begins to form a channel through the heart wall. Tissue severed by cutting head 128 during the process of forming the channel in the heart wall is aspirated through drive tube 126 and flexible hose 117 and collected in trap 114 of vacuum source 113.

At point $t_2$ during travel of cutting head 128 through the heart wall, the cutting head pierces the endocardium. This event is expected to be accompanied by a slight increase in the pressure (point $P_2$ in FIG. 14) as aspiration of severed tissue is replaced by blood from the ventricle. Applicant expects that piercing of the endocardium may be sensed by the clinician as reduced pressure to continued compression of handle assembly 130. Additionally, this event may be detected from a visual display of the instantaneous pressure.

Once the endocardium is punctured, the clinician depresses footpedal switch 120 to supply a burst of RF energy from RF energy source 115 to electrode 160 and cutting head 128, thereby cauterizing the tissue forming the walls of the channel. At time $t_3$, trumpet valve 141 is depressed to relieve the negative pressure in suction cup 129 (point $P_3$ in FIG. 14), and the compressive force applied to handle assembly 130 is released. When the clinician releases the compressive force applied to handle assembly 130, spring 151 retracts cutting head 128 from the channel formed in the heart. As spring 151 urges cradle 125 in the proximal direction, cradle 125 contacts motion switch 154, deactivating motor 124. Applicant expects that extension and retraction of cutting head 128 may be readily accomplished during diastole of a single cardiac cycle (i.e., within about one second).

The clinician then repositions the distal end of device 111 to an adjacent region of the epicardium and repeats the process. Applicant expects that 20 to 30 transmural channels, each about 1 mm to 5 mm in diameter, may be formed in the heart in about five minutes or less, and will provide improved myocardial perfusion.

Referring now to FIGS. 15A to 15F, different modalities of operation of a cutting head constructed in accordance with the present invention are described. In FIGS. 15A–15F, various cutting heads are described as illustratively constructed from a sharpened tubular member, similar to that described with respect to FIG. 13B. All of the embodiments of FIGS. 15A to 15E described hereinbelow preferably include a central lumen that may be coupled to a vacuum source for aspirating tissue severed by the cutting head from the treatment site, thus reducing the risk of embolization.

Figure 15A:
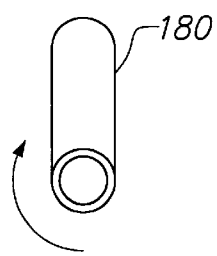
FIGS. 15A to 15F are perspective views, partly in block diagram form, illustrating different cutting modalities suitable for use with apparatus constructed in accordance with the present invention.
Figure 15B:
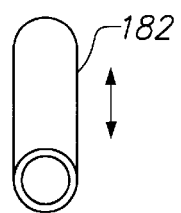
Figure 15C:
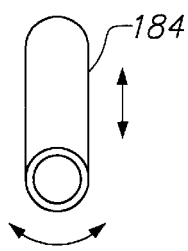

In FIG. 15A, cutting head 180 is arranged for rotary motion, like cutting head 128 described with respect to FIG. 13B. Cutting head 180 is moved in the proximal and distal directions by actuation of handle assembly 130. In FIG. 15B, cutting head 182 is arranged for rapid reciprocation in the distal and proximal directions, which motion is superimposed on the distal and proximal motion of the cutting head caused by actuation of the handle assembly. In FIG. 15C, cutting head 184 is reciprocated rapidly in the longitudinal direction while experiencing rapidly alternating angular motion of several degrees, for example, 90 to 120 degrees, which motion is again superimposed on the overall distal and proximal motion caused by compression of handle assembly 130.

Figure 15D:
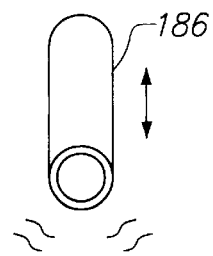

In FIG. 15D, cutting head 186 is vibrated at high frequency, either in the longitudinal direction, an angular direction, or both, to cause emulsification of the tissue contacted by the cutting head. Vibration of cutting head 186 may be accomplished either by a mechanical gear driven arrangement, or may be provided by an ultrasonic device. In either case, the vibratory motion of the cutting head is in addition to motion in the distal and proximal directions caused by actuation of handle assembly 130.

Figure 15E:
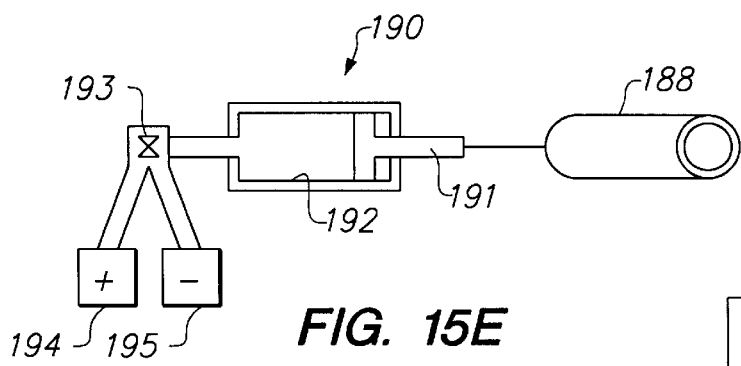

In FIG. 15E, cutting head 188 is described together with actuator 190. Cutting head 188 is advanced at very high speed in the distal direction, for example, by a hydraulic actuator, to pierce the heart tissue in a single motion. In this embodiment, drive tube 126 need not be rotated, and motor 124 of the embodiment of FIG. 12 is replaced by actuator 190 comprising piston 191 that reciprocates within cylinder 192, valving 193 that selectively couples piston 191 to source of high pressure 194 (e.g., a cylinder of pressurized gas) and a source of low pressure 195 (e.g., vacuum source 113).

Figure 15F:
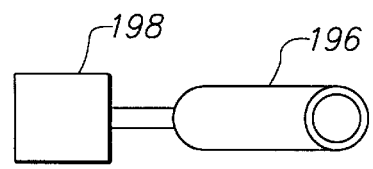

In FIG. 15F, a yet further alterative embodiment of a cutting head constructed in accordance with the present invention is described. Cutting head 196 comprises a nozzle through which fluid, for example, saline, is ejected at high pressure, for example 1000 psi. The fluid stream impinges upon and cuts a channel in the tissue. In this embodiment, drive tube 126 remains stationary and motor 124 is replaced by a high pressure hydraulic pump 198.

Figure 16A:
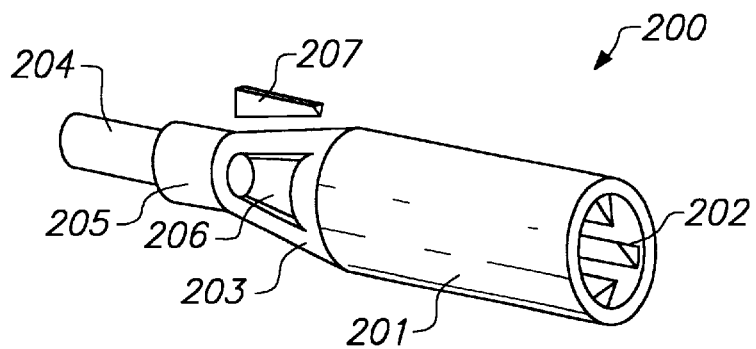
FIGS. 16A to 16D are sectional and perspective views of various cutting heads constructed in accordance with the present invention.

Referring now to FIGS. 16A to 16D, illustrative examples of rotary cutting heads are described. In FIG. 16A, cutting head 200 includes tubular region 201 having a sharp beveled edge and a plurality of angled teeth 202 disposed from its interior wall. Frustoconical portion 203 joins tubular region 201 to drive cable 204 via hub 205. Frustoconical portion 203 has openings 206 through which tissue severed by teeth 202 within tubular region 201 exit into the lumen of drive tube 126.

Cutting head 200 provides the capability to further divide the severed tissue after it is cut from the heart wall by teeth 202. Teeth 202 preferably are sharp slanted blades mounted on the interior wall of tubular member 201, and are arranged so that they urge the severed tissue in the proximal direction when cutting head 200 is rotated (in conjunction with action of the negative pressure in drive tube 126 and forward movement of the cutting head). As the tissue exits tubular region 201 by passing through windows 206, the tissue is further finely divided by the arms of frustoconical region 203 that connect tubular region 201 to hub 205. Because cutting head 200 is rotated at high speeds, the severed tissue is finely divided by region 203, enhancing the ease with which the tissue may be aspirated.

Cutting head 200 may optionally include two or more stationary blades 207 (one shown in FIG. 16A), which are preferably fixed to the interior of drive tube 126. Tissue exiting windows 206 of cutting head 200 impinge upon stationary blades 207, which further finely divide the tissue. Applicant expects that such morcellation of the severed tissue will further enhance the ability to aspirate the tissue.

Figure 16B:
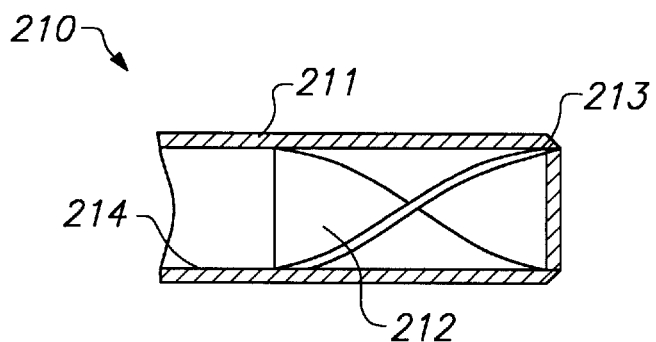

In FIG. 16B, cutting head 210 comprises tubular region 211, which may comprise the distal end of drive tube 126, within which blade 212 is disposed. Distal edge 213 of tubular element 211 includes a sharpened bevel. Blade 212 is located immediately below, or flush with, distal edge 213 of tubular element 211, and is formed of, for example, a tough plastic, nylon, or metal or alloy, such as stainless steel.

Blade 212 preferably consists of one turn of a double helix and is designed to cut tissue that protrudes into tubular element 211. Cutting head 210 is affixed to tubular region 211 so that the helix of blade 212 is rotated in a direction suitable for pushing severed tissue into the lumen of tubular member 211. Alternatively, blade 212 may have a propeller-like shape that includes sharpened edges for severing tissue drawn into tubular member 211, for example, by suction or forward motion of the tubular member.

Figure 16C:
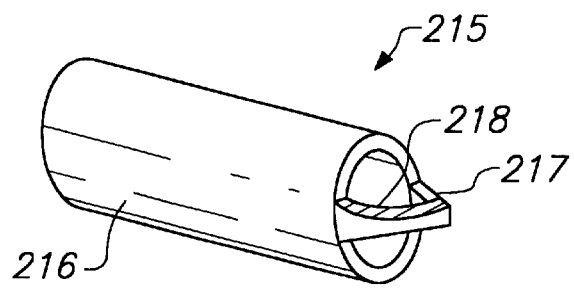

In FIG. 16C, cutting head 215 comprises tubular member 216 carrying band-type blade 217. Blade 217 projects from the distal end face of tubular member 215, and includes a band or ribbon having sharpened lead edges 218. Blade 217 may be affixed to the distal end of drive tube 126 by any suitable means, for example, threads, welding or rivets.

Figure 16D:
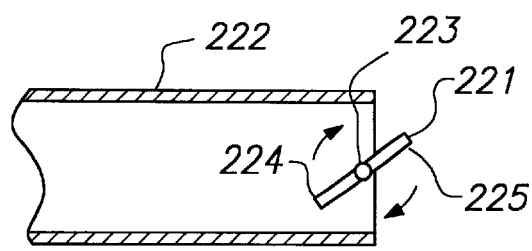

In FIG. 16D, cutting head 220 comprises circular hoop 221 disposed in tubular member 222 for rotation about pin 223. Tubular member 222 may comprise the distal end of drive tube 126. Hoop 221 preferably comprises a band of high strength material having sharpened leading edges 224 and 225. When rotated by drive means (not shown), for example, a worm screw or flexible cable, hoop 221 scoops out tissue that comes into contact with the cutting head. In this embodiment, drive tube 126 need not be configured for rotation.

Figure 17A:
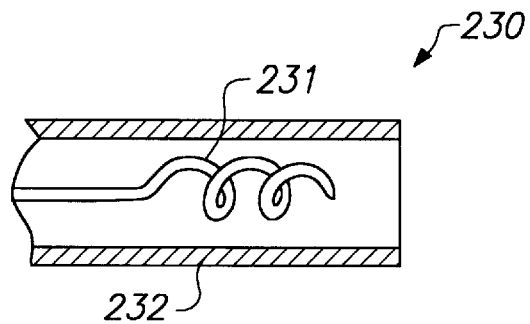
Figure 17B:
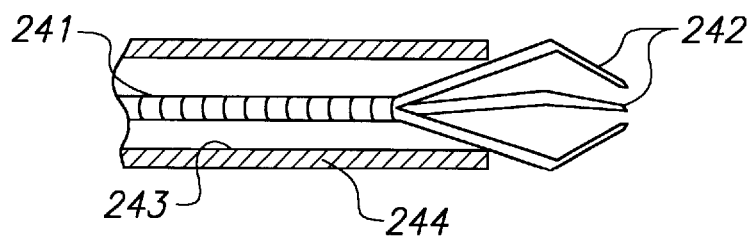
Figure 17C:
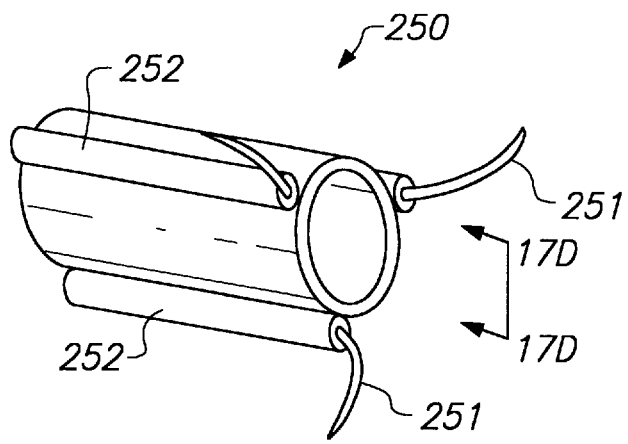

Referring now to FIGS. 17A to 17C, alternative embodiments of stabilizing means for use in the apparatus of the present invention are described. It is contemplated that stabilizing means 230 may be substituted for suction cup 129 of the embodiment of FIGS. 13, and provide engagement of the cutting head to the heart during the step of forming a channel through the heart wall.

In FIG. 17A, stabilizing means 230 comprises sharpened corkscrew element 231 disposed in tubular member 232. Corkscrew element 231 may be located on the distal end of shaft 127 adjacent to cutting head 128 (in place of suction cup 129), and may be rotated by a suitable drive rod and knob on housing 123 to pierce the epicardium and urge the cutting head in contact with the heart during the channel forming process. Alternatively, corkscrew element 231 may be disposed on a drive rod within, and form a part of, the cutting head. In this case, corkscrew element 231 will serve not only to stabilize the cutting head in contact with the tissue, but will also serve to draw the tissue into the cutting head, thus reducing risk of embolization.

In FIG. 17B, stabilizing means 240 is in the form of shaft 241 having resilient fingers 242 disposed on it. Stabilizing means 240 is located on the distal end of shaft 127 adjacent to cutting head 128 (in place of suction cup 129). Shaft 241 and fingers 242 are disposed in lumen 243 of tubular member 244, so that when shaft 241 is urged in the distal direction, fingers 242 open away from one another. Shaft 241 is biased in the distal direction within tubular member 244 so that the tips of fingers 242 are located near one another. Accordingly, to engage stabilizing means 240 with the epicardium, a knob (not shown) on the housing 123 is pushed in the distal director, so that fingers 242 are spread apart. Fingers 242 are then brought into contact with the epicardium, and shaft 241 is released against its spring bias, so that fingers 242 pinch the epicardium. Upon completion of the channel forming process, shaft 241 is pushed and held in the distal direction so as to release the grip of fingers 242 on the epicardium.

Figure 17D:
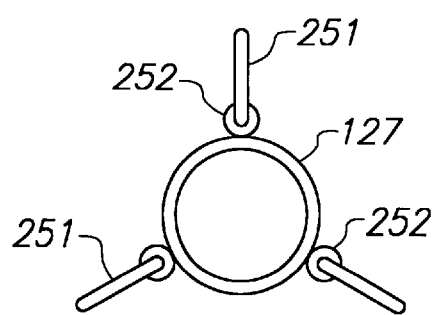
FIG. 17D is a cross-sectional view of the stabilizing means of FIG. 17C taken along view line 17D—17D of FIG. 17C.

With respect to FIGS. 17C and 17D, a further alternative embodiment of stabilizing means constructed in accordance with the present invention is described. Stabilizing means 250 comprises a plurality of resilient curved wires 251 having sharpened tips that are disposed in lumens 252 spaced apart around the periphery of shaft 127. Curved wires are connected to a button (not shown) on housing 123, that permits wires 251 to be moved in the distal and proximal directions. Wires 251, which preferably comprise a shape memory material, such as a nickel-titanium alloy, diverge radially outward when extended distally from lumens 252. Thus, when the distal end of device 111 is brought into contact with the epicardium, the button may be actuated to move wires 251 in the distal direction. As wires 251 are extended from lumens 252, the tips of the wires pierce the epicardium and spread away from one another, thereby drawing the cutting head into contact with the tissue. Upon completion of the channel forming process, wires 251 are retracted into lumens 252 to release the tissue.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. Apparatus for use for performing transmyocardial revascularization by cutting a channel in cardiac tissue, the apparatus comprising:

a housing, a shaft coupled to the housing, the shaft including a lumen and a distal endface;

an end effector disposed within the shaft for cutting a channel in the cardiac tissue, the end effector selectively movable from a first position disposed within the shaft to a second position wherein the end effector is extended beyond the distal endface, a stabilizing element disposed on the shaft that stabilizes the cardiac tissue against the end effector to counteract wall motion of the cardiac tissue;

means for drawing a level of suction through the end effector to aspirate cardiac tissue severed by the end effector;

control circuitry for monitoring the level of suction and generating a signal; and a linear actuator mechanism that controls movement of the end effector between the first and second positions responsive to the signal.

2. The apparatus as defined in claim 1 further comprising means for cauterizing the cardiac tissue surrounding the channel.

3. The apparatus as defined in claim 2 wherein the means for cauterizing comprises an RF energy source and at least one electrode disposed on the shaft for applying RF energy to the cardiac tissue surrounding the channel.

4. The apparatus as defined in claim 2 wherein the means for cauterizing comprises an exterior surface of the end effector, the end effector moved in relation to the cardiac tissue surrounding the channel so as to frictionally generate heat that cauterizes the cardiac tissue.

5. The apparatus as defined in claim 4 wherein motion of the end effector is selected from the group consisting of reciprocatory motion, angular motion or vibrational motion.

6. The apparatus as defined in claim 1 wherein the end effector includes a cutting head, the apparatus further comprising a motor disposed within the housing and coupled to the cutting head to rotate the cutting head.

7. The apparatus as defined in claim 1 wherein the linear actuator mechanism comprises a handle assembly and a motion switch, the motion switch configured to activate the motor when the handle assembly is actuated.

8. The apparatus as defined in claim 1 wherein the linear actuator mechanism comprises:

a motor;

a lead screw coupled to the motor; and means for coupling the lead screw to the end effector.

9. The apparatus as defined in claim 1 wherein the stabilizing element comprises a suction cup disposed on the shaft near the end effector and means for inducing suction through the suction cup.

10. The apparatus as defined in claim 9 wherein the means for drawing suction through the end effector provides a first level of suction to the end effector and the means for inducing suction through the suction cup provides a second level of suction, the second level lower than the first level.

11. The apparatus as defined in claim 1 wherein the stabilizing element comprises:

a tubular member defining a passageway;

a shaft disposed within the passageway, the shaft having a distal end and a plurality of resilient outwardly directed fingers disposed on the distal end, the shaft biased in the passageway so that the outwardly directed fingers are disposed adjacent one another, wherein, when the shaft is displaced in a distal direction, the outwardly directed fingers move apart to grip the cardiac tissue.

12. The apparatus as defined in claim 1 wherein the stabilizing element comprises:

a corkscrew element; and means for rotating the corkscrew element to pierce and engage the cardiac tissue.

13. The apparatus as defined in claim 1 wherein the stabilizing element comprises:

a tubular member defining a passageway;

a wire having a sharpened tip, the wire disposed for movement through the passageway from a first position wherein the wire is retracted within the passageway to a second position wherein the wire is extended from the passageway, the wire having a curved form in the second position that retains the end effector in contact with the cardiac tissue.

14. The apparatus as defined in claim 1 wherein the end effector comprises:

a cutting head and the apparatus further comprises means for rotating the cutting head.

15. The apparatus as defined in claim 14 further comprising a drive tube having a distal end coupled to the cutting head and a proximal end coupled to the means for drawing suction through the end effector.

16. The apparatus as defined in claim 15 wherein the drive tube and cutting head are disposable.

17. The apparatus as defined in claim 15 wherein the drive tube comprises:

a rigid proximal portion;

a rigid distal portion; and a flexible drive coupling disposed between the rigid proximal portion and the rigid distal portion.

18. The apparatus as defined in claim 15 wherein the means for drawing suction induces suction through the drive tube and the drive tube comprises a portion formed of a coil spring having closely spaced adjacent turns, the apparatus further comprising an angled sleeve having a portion defining a lumen, the coil spring being disposed within the lumen so that the drive tube passes through the angled sleeve without substantial loss of suction.

19. The apparatus as defined in claim 14 wherein the cutting head comprises:

a tubular member having an interior passage in communication with the lumen.

20. The apparatus as defined in claim 19 wherein the cutting head further comprises a helical blade disposed within the tubular member.

21. The apparatus as defined in claim 19 wherein the cutting head has a distal end and a proximal end, and the interior passage of the cutting head has a diameter that increases from the distal end to the proximal end.

22. The apparatus as defined in claim 19 wherein the tubular member further comprises a raised thread disposed in the interior passage, the raised thread oriented so that the raised thread pushes severed cardiac tissue in a proximal direction as the cutting head rotates.

23. The apparatus as defined in claim 19 wherein the tubular member includes a distal end, and the cutting head further comprises a sharpened band projecting from the distal end.

24. The apparatus as defined in claim 19 wherein the cutting head comprises:

a tubular portion having a proximal end, an interior passage and an interior surface;

a plurality of teeth disposed from the interior surface;

a frustoconical portion coupled to the proximal end of the tubular portion, the frustoconical portion including portions defining windows the enable cardiac tissue collected in the interior passage to pass into the lumen; and a hub for coupling the cutting head to the means for rotating.

25. The apparatus as defined in claim 19 wherein the means for rotating comprises:

a motor; and a drive shaft coupled between the motor and the hub, the drive cable disposed within the lumen.

26. The apparatus as defined in claim 1 wherein the end effector comprises a sharpened tube, the apparatus further comprising means for advancing the sharpened tube at high speed in a distal direction.

27. The apparatus as defined in claim 1 wherein the end effector comprises a tubular member and means for ejecting a fluid stream from the tubular member at high speed.

28. Apparatus for use for performing transmyocardial revascularization by cutting a channel in cardiac tissue, the apparatus comprising:

a housing, a shaft coupled to the housing, the shaft including a lumen and a distal endface;

an end effector disposed within the shaft for cutting a channel in the cardiac tissue, the end effector selectively movable from a first position disposed within the shaft to a second position wherein the end effector is extended beyond the distal endface;

a stabilizing element disposed on the shaft that stabilizes the cardiac tissue against the end effector to counteract wall motion of the cardiac tissue;

means for drawing suction through the end effector to aspirate cardiac tissue severed by the end effector;

control circuitry for monitoring a displacement of the end effector and generating a signal; and a linear actuator mechanism that controls movement of the end effector between the first and second positions responsive to the signal.

29. The apparatus as defined in claim 28 further comprising means for cauterizing the cardiac tissue surrounding the channel.

30. The apparatus as defined in claim 28 wherein the end effector includes a cutting head, the apparatus further comprising a motor disposed within the housing and coupled to the cutting head to rotate the cutting head.

31. The apparatus as defined in claim 28 wherein motion of the end effector is selected from the group consisting of reciprocatory motion, angular motion or vibrational motion.

32. The apparatus as defined in claim 28 wherein the end effector comprises:

a cutting head and the apparatus further comprises means for rotating the cutting head.

33. The apparatus as defined in claim 32 further comprising a drive tube having a distal end coupled to the cutting head.

34. The apparatus as defined in claim 33 wherein the drive tube and cutting head are disposable.

35. The apparatus as defined in claim 33 wherein the drive tube comprises:

a rigid proximal portion;

a rigid distal portion; and a flexible drive coupling disposed between the rigid proximal portion and the rigid distal portion.

36. The apparatus as defined in claim 33 wherein the means for drawing suction induces suction through the drive tube and the drive tube comprises a portion formed of a coil spring having closely spaced adjacent turns, the apparatus further comprising an angled sleeve having a portion defining a lumen, the coil spring being disposed within the lumen so that the drive tube passes through the angled sleeve.

\* \* \* \* \*